(12) United States Patent
Kirby et al.

(10) Patent No.: US 7,179,422 B2
(45) Date of Patent: Feb. 20, 2007

(54) APPARATUS FOR IMPROVED DETECTION OF CARBON MONOXIDE BY INFRARED ABSORPTION SPECTROSCOPY

(75) Inventors: Kevin W. Kirby, Calabasas Hills, CA (US); Amanda C. Phelps, Malibu, CA (US); Robert N. Schwartz, Costa Mesa, CA (US)

(73) Assignee: HRL Laboratories, LLC, Malibu, CA (US)

( * ) Notice: Subject to any disclaimer, the term of this patent is extended or adjusted under 35 U.S.C. 154(b) by 269 days.

(21) Appl. No.: 10/387,004

(22) Filed: Mar. 11, 2003

(65) Prior Publication Data

US 2003/0166294 A1    Sep. 4, 2003

Related U.S. Application Data

(62) Division of application No. 09/691,793, filed on Oct. 18, 2000, now Pat. No. 6,645,772.

(51) Int. Cl.
    G01N 21/00    (2006.01)
(52) U.S. Cl. .................. 422/82.05; 422/55; 422/67
(58) Field of Classification Search ............ 422/82.05, 422/55, 78; 436/133, 134
    See application file for complete search history.

(56) References Cited

U.S. PATENT DOCUMENTS

| | | | |
|---|---|---|---|
| 3,757,572 A | | 9/1973 | Gower et al. |
| 3,758,666 A | | 9/1973 | Frevel et al. |
| 3,977,813 A | * | 8/1976 | Bustard et al. ............... 417/49 |
| 4,030,887 A | * | 6/1977 | Poli et al. ................... 436/134 |
| 4,290,878 A | * | 9/1981 | Blanton, Jr. ............ 208/120.35 |
| 4,668,635 A | | 5/1987 | Forster |
| 4,808,564 A | | 2/1989 | Matsumoto et al. |
| 4,816,749 A | | 3/1989 | Schmidtpott et al. |
| 4,943,550 A | | 7/1990 | Kolts et al. |
| 5,550,093 A | * | 8/1996 | Wan et al. ................... 502/74 |
| 5,896,088 A | | 4/1999 | Brooks, Jr. |
| 5,968,217 A | * | 10/1999 | Stein et al. ................... 55/496 |
| 6,003,307 A | | 12/1999 | Naber et al. |

FOREIGN PATENT DOCUMENTS

JP         55008827 A  *  1/1980

OTHER PUBLICATIONS

Hofland et al."Effect of CO2 on the Performance of Au/MnOx and Pt/SnOx.Low-Temperature CO Oxidation Catalysts", Langmuir, 1995, v. 11, pp. 3431-3434.*

(Continued)

Primary Examiner—Yelena G. Gakh
(74) Attorney, Agent, or Firm—Ladas & Parry LLP

(57) ABSTRACT

A method for detecting the presence and amount of carbon monoxide, comprising the use of infrared spectroscopy to compare the spectra of the test gas containing carbon monoxide and the reference gas. The reference gas is the test gas from which carbon monoxide had been removed by conversion using catalysts. The presence and quantity of carbon monoxide is determined by deducting the spectrum of the reference gas from the spectrum of the test gas. The catalysts comprise nanoparticles of gold precipitated on a metal oxide or hydroxide carrier. An apparatus implementing this method.

16 Claims, 3 Drawing Sheets

OTHER PUBLICATIONS

"Ozone in Ambient Air Analayer. Model 427", http://www.users.globalnet.co.uk/~signal/Data_sheets/Ds130800.pdf, Aug. 2000.*

Sanchez et al. "When Gold Is Not Noble: Nanoscale Gold Catalysts", Journal of Physical Chemistry A, 1999, v. 103(48), pp. 9573-9578.*

Colthup, Norman B., et al. "Introduction to Infrared and Raman Spectroscopy", Academic Press, New York and London, 1964, pp. 74-77.

Finch, Rowan M., et al., "Identification of active phases in Au—Fe catalysts for low-temperature CO oxidation", *Phys. Chem. Chem. Phys.*, 1999, 1, 485-489, pp. 485.

Haruta, Masatake, "Low-Temperature Oxidation of CO over Gold Supported on $TiO_2$, $\alpha$—$Fe_2O_3$, and $Co_3O_4$", Journal of Catalysis 144, 175-192 (1993), Academic Press, Inc., 1993, p. 175.

Haruta, Masatake, "Novel catalysis of gold deposited on metal oxides", Osaka National Research Institute, AIST, Midorigaoka Jan. 8, 1931, Ikeda 563, Japan, Catalysis Surveys of Japan 1(1997) 61-73, Baltzer Science Publishers BV, p. 61.

Kahlich, M.J., et al., "Kinetics of the Selective Low-Temperature Oxidation of CO in $H_2$—Rich Gas over Au/$\alpha$—$Fe_2O_3$", http://www.uni-ulm.de/aok/Papers/mike/index.html, p. 1.

"Model 6600 Miniature Automotive Gas Analyzer", 6600 Product Manual, ANDROS Incorporated, Berkeley, California, p. ii and 25.

Sakurai, Hiroaki, et al., "Low-temperature water-gas shift reaction over gold deposited on $TiO_2$", Osaka National Research Institute, AIST, Midorigaoka 1, Ikeda, Osaka 563, Japan, p. 271 of *Chem. Commun.*, 1997.

"The Mechanism of the Catalytic Action of Platinum in the Reactions $2CO+O_2=2CO_2$ and $2H_2+O_2=2H_2O$", Transactions of the Faraday Society, vol. XVII Part 3, 621, 1921, p. 295.

Tsubota, Susuma, et al., "Preparation of Highly Dispersed Gold on Titanium and Magnesium Oxide", Government Industrial Research Institute of Osaka Midorigaoka 1, IKEDA 563, Japan, from *Preparation of Catalysts V*, edited by G. Poncelet, et al., Elsevier Science Publishers B.V., Amsterdam, 1991, p. 695.

* cited by examiner

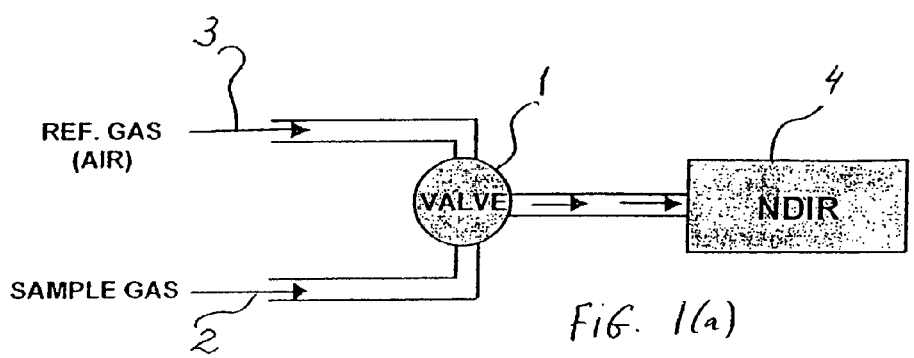
PRIOR ART
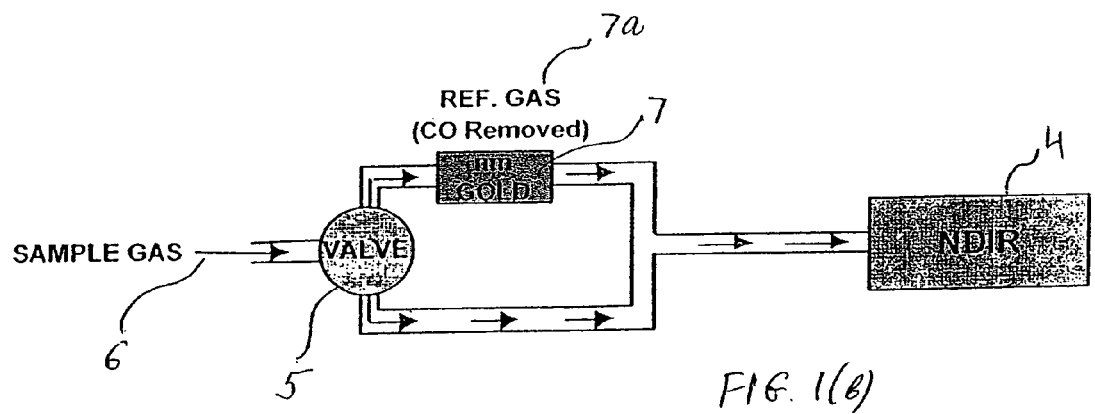

APPARATUS FOR IMPROVED DETECTION OF CARBON MONOXIDE BY INFRARED ABSORPTION SPECTROSCOPY

This is a divisional of U.S. application Ser. No. 09/691,793, filed on Oct. 18, 2000, now U.S. Pat. No. 6,645,772.

I. BACKGROUND OF THE INVENTION

1. Field of the Invention

This invention relates to the field of the detection of carbon monoxide. More particularly, it pertains to the use of infrared absorption spectroscopy for such detection. A method of detection and measuring proposed hereinafter is simple, inexpensive, accurate and allows for the measurements to be conducted in the field, outside of a laboratory environment.

2. Description of the Related Art

One of the most important technological processes is the production of hydrogen on site, via a reformation process involving the reaction of water with methanol. Among other applications, this process is used, for instance, in the development of fuel cells where hydrogen so produced serves as fuel. The reformation process not only produces a fuel cell feed stream containing hydrogen, but also such by-products as carbon dioxide and small amounts of carbon monoxide.

The carbon monoxide constituent has the effect of poisoning the fuel cell at levels as low as 10 parts per million. Carbon monoxide is also known to be a harmful by-product, even when present in very small concentrations, in other processes and applications. Therefore, a method and apparatus for measuring and/or monitoring the concentration of carbon monoxide at levels of about 10 parts per million is desired.

Presently, the only reliable technique for sensing carbon monoxide at these levels is by infrared absorption spectroscopy. However, to resolve species at very low levels, the intrinsic drift of the instrument and the interference from other species present in large concentrations (such as, in this case, carbon dioxide which can occur in the amount of 18% by volume) or water present in large concentrations must be eliminated or compensated for during the measurement.

Currently, to compensate for the drift, the instrument is periodically put through a zeroing procedure using an internal standard as the zero reference material. See, e.g., N. Colthup, et. al., *Introduction to Infrared and Raman Spectroscopy*, Academic Press, New York, 1964, pp. 74–77. In many cases, the standard reference gas used is ambient air.

While air provides a reference absent of carbon monoxide, it does not address the compensation for the interfering gases. An additional problem is that the concentration of the interfering gases is dynamic, thereby not allowing a fixed compensation to be built into the measurement system.

The zeroing procedure involves a technique of subtracting a reference gas absorption spectrum from a sample gas absorption spectrum to obtain a third spectrum where the contribution of species common to both gases has been eliminated. Such technique is known in the prior art. See, e.g., *Model 6600 Miniature Automotive Gas Analyzer*, Andros Incorporated's Product Manual.

In a laboratory environment, the reference process typically consists of performing a calibration measurement with a gas mixture that has a known concentration of the species to be measured, and another measurement with a gas mixture that does not contain the species. The gas mixture that does not contain the species is used to set the zero point for the instrument, and usually consists of room air. The reference gas that contains the species to be measured is preferably similar in composition to the sample gas mixture, such that potential interference from several gas species absorbing in similar wavelength regions is accounted for during the measurement.

In the field, or non-laboratory environment, periodic calibration of the instrument with two separate gases is typically not practicable. This two-reference gas calibration technique refers to a method by which the zero point and the span of the infrared instrument are calibrated. The zero point refers to the level whereby the instrument decides that the concentration of a measured gas is zero. The span refers to calibrating the instrument with a specific concentration of the gas species to be measured.

An example of the use of two-reference gas calibration technique would be exposing the instrument to a gas containing 100 parts per million (ppm) carbon monoxide, and then referencing future measurements to the amount of signal obtained at each level.

At best, an initial calibration with the two gases is performed, followed by periodic zero point references with room air. This technique is found to be somewhat useful in preventing large measurement errors introduced by baseline or zero point drift, but does not address errors introduced by the dynamic concentration of interfering species in the sample gas. When a high measurement accuracy (±5–10 ppm) is required in the under 100 parts per million range for a given species, the measurement error introduced by the interfering species must be somehow compensated for during the measurement.

However, no known prior art which involves the use of infrared absorption spectroscopy coupled with the zeroing technique allows for accurate detection of carbon monoxide at the very low concentrations mentioned above, especially for outside-of-the-laboratory use.

As will be subsequently discussed, the method proposed in this invention utilizes a catalyst to remove carbon monoxide from the feed stream, via its oxidation to carbon dioxide, with the subsequent use of the remaining feed stream gas as a zero reference. A catalyst is, therefore, needed that operates to efficiently remove carbon monoxide from the feed stream at low temperatures, namely as low as the normal operating temperature of the system (about 80° C.).

Previously developed catalysts for carbon monoxide oxidation include a commercially available, manganese oxide and copper oxide-based Hopcalite, and platinum or palladium-supported structures on oxide hosts. These catalysts depend on the presence of oxygen to form carbon dioxide from carbon monoxide, and require temperatures in the range of 150–350° C. to achieve high efficiency.

Furthermore, these catalysts exhibit a low degree of selectivity towards carbon monoxide oxidation in the presence of hydrogen. Such use of platinum catalysts for conversion of carbon monoxide into carbon dioxide is described, for example, in *The Mechanism of the Catalytic Action of Platinum in the Reactions $2CO+O_2=2CO_2$ and $2H_2+O_2=2H_2O$*, Transactions of the Faraday Society, vol. XVII, Part 3, 621 (1921).

Other known catalysts that require only water to form carbon dioxide from carbon monoxide include iron oxide structurally in combination with chromium oxide, and copper/zinc oxide/aluminum oxide formulations. The iron oxide-chromium oxide catalyst, however, requires temperatures in the range of 300–450° C. and pressures exceeding 2.5 MPa. The copper/zinc oxide/aluminum oxide catalyst also requires temperatures higher than 110° C. See, e.g., H.

Sakurai, et. al., *Low Temperature Water-Gas Shift Reaction Over Gold Deposited on $TiO_2$*, Chem. Commun., p. 271 (1997).

In view of the foregoing, there is a need for a simple, inexpensive and accurate method for detection of carbon monoxide in an environment, including a fuel cell environment, which method would allow for the measurements to be conducted in the field.

The present invention proposes such method based on the periodic zeroing routine of the instrument, but improves upon the compensation process by using the actual feed stream gas, from which carbon monoxide has been removed, as the zero reference. With this technique, accurate detection of carbon monoxide in the 10 parts per million range can be realized.

Furthermore, there is a need for a catalyst which would allow such new method to be realized. Certain important feed streams operate at temperatures as low as about 80° C. and contain an abundance of water and hydrogen, with very small amounts of oxygen. It is therefore important that the catalyst be able to operate at low temperatures and be specific towards carbon monoxide oxidation when either oxygen or water is the available oxidizing agent. None of the existing catalysts mentioned above is satisfactory. New catalysts are needed which have this ability, and therefore offer an advantage over the other stated catalysts. Such catalysts are also taught in this invention.

II. SUMMARY OF THE INVENTION

Infrared absorption spectroscopy is a useful analytical tool for determining the presence and concentration of a particular gaseous species in a flowing mixed gas stream. Consequently, this technique has been suggested as a means by which to measure the amount of carbon monoxide present in reformate gas streams, including those reformate gas streams intended to power a hydrogen-based fuel cell.

Many gas molecules exhibit a moderate to strong absorption at one or more characteristic wavelengths in the infrared area of the spectrum. Devices that measure the amount of absorption at one or more of the characteristic wavelengths can therefore be used to determine the presence of the gaseous species in the stream.

Existing methods for such measurements are, however, seriously flawed. Difficulties encountered when implementing this type of analysis include interference from other species present in the reformate gas stream, such as carbon dioxide and water. Both these species absorb in the same wavelength region as the target species, limiting the quantitative accuracy of the measurement. In particular, water, carbon monoxide and carbon dioxide all absorb very strongly in the infrared area. Both CO and $CO_2$ have characteristic absorption frequencies at 1600–1820 $cm^{-1}$ (C=O bonds) and 1050–1290 $cm^{-1}$ (C—O bonds). Water also absorbs at 1600–1780 $cm^{-1}$. Detecting the presence, and accurate measurement of the concentration, of carbon monoxide is thus seriously impeded because both water and carbon dioxide mask carbon monoxide. Other species often present in the reformate gas stream also absorb in the same area of the spectrum and play similar masking roles.

In a laboratory environment, calibration gases are used to set the zero point reference and span for the instrument to compensate for interference effects. However, for end use applications of the device outside the lab, such as on a fuel cell powered vehicle, these types of calibration procedures are unavailable. It is therefore desirable to develop a simple and inexpensive method by which potentially interfering species such as carbon dioxide and water can be compensated for during the measurement of carbon monoxide.

The present invention describes a method and an apparatus by which the sample gas to be measured is treated in a manner whereby it can be sequentially used as a reference gas, providing a means of self-calibration for the infrared spectroscopic instrument.

More specifically, the sample gas containing carbon monoxide (target species), carbon dioxide and water (interfering gases), and other gases such as hydrogen, nitrogen, and oxygen (non-interfering gases), are passed through a reactive catalyst bed at the normal operating temperature of the gas stream of preferably between about 70° C. and about 80° C. The operating temperature of the system can be as low as room temperature of about 20° C.

The catalyst acts to effectively and selectively remove the carbon monoxide from the stream, producing a gas stream that is nearly identical in composition to the sample gas with the exception of the carbon monoxide constituent. This new gas stream is then used as the zero point reference during the instrument's self-calibration procedure. Since the reference gas contains the interfering gases at practically the same or nearly the same concentration as the sample gas, their contribution to the net infrared absorption is eliminated by virtue of the zeroing procedure.

As a result, only the contribution from carbon monoxide is observed when measuring the infrared absorption of the sample gas. The method allows to accurately measure very low concentrations of carbon monoxide (as low as 10 parts per million) outside the laboratory. Previous attempts at utilizing infrared spectroscopy in the form of an in-field sensor, for instance, an on-board sensor in a vehicle, have failed because of the interference phenomena by other gases in the feed stream.

The method can be applied to a fuel cell system and the detecting device utilizing the method can be installed on board a vehicle. The specific application of the infrared detection method, which incorporates the zeroing procedure, to a fuel cell system, and the low temperature catalyst used to create the reference gas are novel.

The invented method comprises the use of a low temperature catalyst used to convert carbon monoxide to carbon dioxide. It has been known for many years that noble metals such as platinum or palladium, either by themselves or when embedded in an oxide host, are efficient catalysts of the reaction of oxidation of carbon monoxide producing carbon dioxide. The drawback of such catalysts is that they require temperatures over 200° C. to become sufficiently active.

More recently, it has been found that nanometer-sized particles of gold embedded or precipitated onto various oxide hosts are extremely efficient catalysts at temperatures as low as −70° C. See, e.g., M. Haruta, *Novel Catalysis of Gold Deposited on Metal Oxides*, Catalysis Surveys of Japan, 1, pp.61–73 (1997); R. M. Finch, et. al., *Identification of Active Phases in Au—Fe Catalysts for Low-Temperature CO Oxidation*, Phys. Chem. Chem. Phys., 1, pp. 485–489 (1999); M. J. Kahlich, et. al. *Kinetics of the Selective Low-Temperature Oxidation of CO in $H_2$-Rich Gas over $Au/\alpha\text{-}Fe_2O_3$*, University of Ulm; M. Haruta, et. al., *Low-Temperature Oxidation of CO over Gold Supported on $TiO_2$, $\alpha\text{-}Fe_2O_3$, and $Co_3O_4$*, Journal of Catalysis, 144, pp. 175–192 (1993); S. Tsubota, et. al., *Preparation of Highly Dispersed Gold on Titanium and Magnesium Oxide*, In G. Poncelet, et. al., Editors, Preparation of Catalysts V, p. 695, Elsevier Science Publishers B. V., Amsterdam, 1991.

Furthermore, these catalysts exhibit good selectivity towards carbon monoxide when in the presence of hydrogen, an important factor considering the large disproportion in concentration between the two gases in the fuel cell feed stream. It is this type of catalyst that has been utilized in the reduction of the present invention to practice.

III. BRIEF DESCRIPTION OF THE DRAWINGS

The features and advantages of the present invention will become better understood with regard to the following description, appended claims, and accompanying drawings where FIGS. 1(a) and 1(b) are schematic diagrams respectively showing existing and improved systems for zero point referencing of a non-dispersive infrared spectroscopic instrument for carbon monoxide measurement. FIG. 1(b) depicts schematically how the present invention can be practiced.

IV. DETAILED DESCRIPTION OF THE INVENTION

Figure 2:
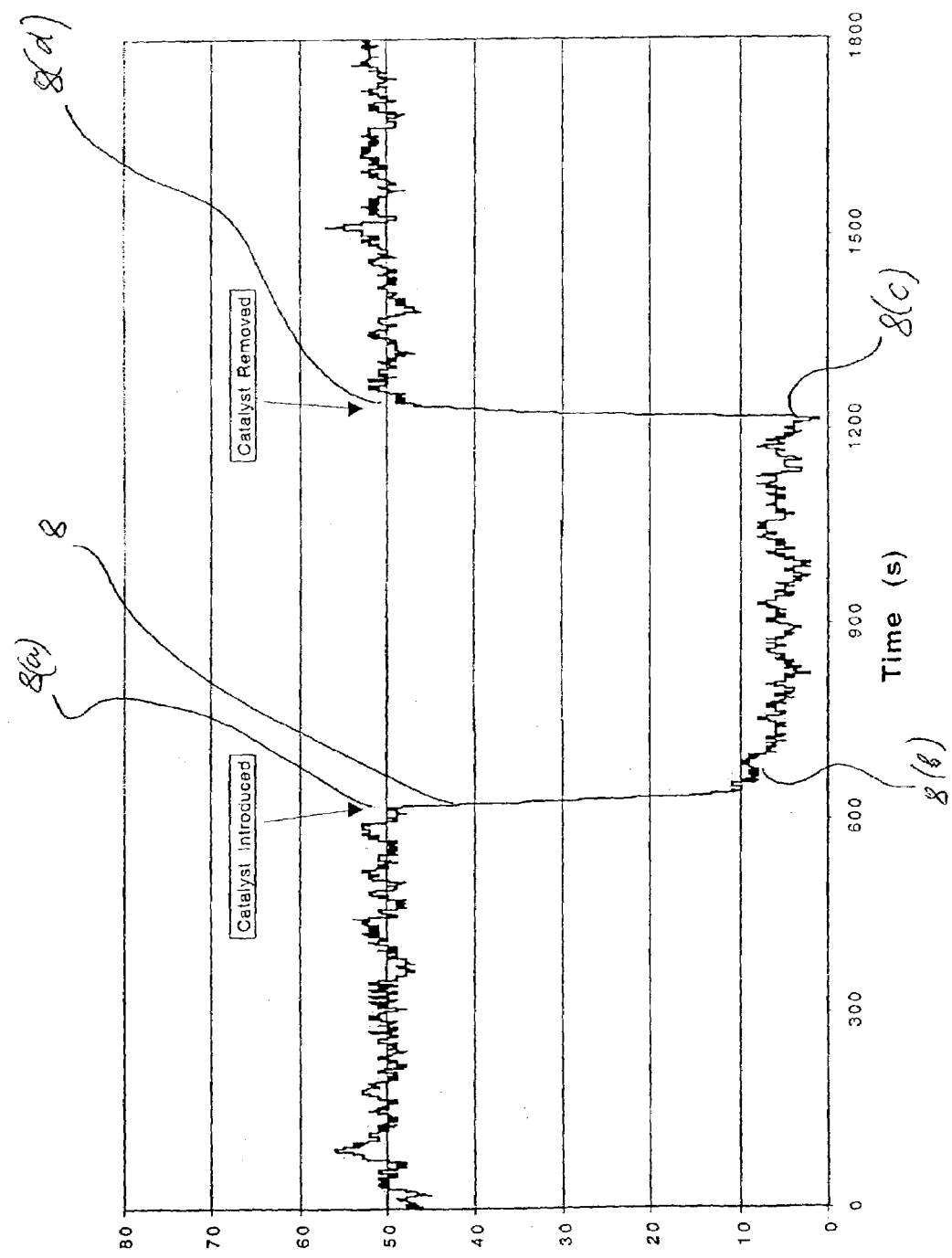
FIG. 2 is a chart showing the results of the measurements of carbon monoxide concentration before and after passing the reformate gas through the catalyst.

1. The Method and the Detector in General.

To quantitatively measure the concentration of the species in the stream, the amount of infrared radiation absorbed by the species at the characteristic wavelength must be compared to a reference or standard.

The present invention is an improvement upon the typical zero point referencing process that a commercially available, portable, infrared spectroscopic instrument utilizes for periodic calibration.

FIGS. 1(a) and 1(b) show the present and improved configurations, respectively, for a nondispersive infrared (NDIR) spectroscopic instrument. Such instruments are commercially available, for example, the Andros Model 6600 instrument, manufactured by Andros Incorporated of Berkeley, Calif.

In the prior art configuration (FIG. 1(a)), a valve 1 switches from the sample gas flow 2 to an air reference 3 during the zeroing process for the instrument 4. The zeroing process consists of making an absorption measurement on the air reference, and arbitrarily setting the observed absorption as the zero level or baseline. The air is from the ambient, and is brought into the instrument 4 by a pump (not shown). The reference or zero point cycle has no set time limit, but can be as short as 10 seconds with this particular NDIR instrument 4.

The improved configuration of FIG. 1(b) makes use of the valve controlled reference process, but eliminates the pumped air source as the reference gas. Instead, the valve 5 directs the sample gas 6 through a catalyst of gold nanoparticles 7 that act to convert the carbon monoxide to carbon dioxide. Since the carbon monoxide concentration is expected to always be below 1,000 parts per million, creation and addition of less than this amount of carbon dioxide to the reference gas 7a from the catalytic conversion process will not affect its overall absorption properties in the infrared area of the spectrum (carbon dioxide is known to already be present in the reference gas at levels near 18% by volume).

After carbon monoxide has been eliminated through the catalyzed conversion into carbon dioxide, the resulting, carbon monoxide-free gas goes through the spectrometer 4 and the latter self-calibrates and memorizes the infrared spectrum of the reference gas 7a. Possibility of such self-calibration is one of the properties of the spectrometer 4. After the spectrometer has been calibrated as described, the valve 5 switches and sample gas 6 is directed to the spectrometer 4. The spectrometer takes the infrared spectrum of the sample gas 6, compares it with the memorized spectrum of the reference gas 7a, subtracts the spectrum of the reference gas 7a from that of the sample gas 6, and the difference shows the presence and the quantity of carbon monoxide.

The calibration process is periodically repeated, preferably, once about every ten minutes. The frequency of calibration can be modified, if desired. The method allows measurement of the amount of carbon monoxide as low as about 10 ppm to about 15 ppm and a data point is produced once about every one second.

The proposed catalysts to be used include, but are not limited to, nanometer-sized gold deposited or precipitated, by co-precipitation, deposition-precipitation, impregnation, or by other common methods known to those skilled in the art, onto particles of iron oxide ($Fe_2O_3$), titanium dioxide ($TiO_2$), nickel oxide (NiO), aluminum oxide($Al_2O_3$), magnesium hydroxide [$Mg(OH)_2$], cobalt oxide ($Co_3O_4$), copper oxide (CuO), manganese oxides ($MnO_x$) and/or iron hydroxides [$Fe(OH)_x$]. All of these catalysts have been shown to be active towards the oxidation of carbon monoxide when in the presence of either oxygen or water, or both, at temperatures below 100° C. Gold is loaded on the oxide hosts preferably in the amounts of between about 1% and about 12% by weight.

2. A Preferred Embodiment.

In a preferred embodiment of the invention, the carbon monoxide detector of this invention is used to detect CO in a fuel cell environment. For such preferred embodiment, as well as for other embodiments where CO is detected in an environment containing water vapor, a preferred catalyst comprises about 11.6% of gold (by weight), precipitated on manganese oxide $MnO_x$ according to a standard co-precipitation technique known to those skilled in the art.

An acceptable alternative, from the list of the catalysts mentioned above, is a catalyst comprised of about 3% gold (by weight) precipitated on iron oxide $Fe_2O_3$, which is also synthesized using a standard co-precipitation process known to those skilled in the art. Such alternative catalyst is less preferred for the detector working in a fuel cell environment or other water-vapor rich environments. Other catalysts mentioned above can also be used, if desired.

A small amount (between about 100 mg and about 500 mg) of the catalyst is packed into a small diameter (between about 4 mm and about 10 mm) quartz tube with quartz wool at either end. The tube is wrapped with heating tape and elevated to temperatures between about 20° C. and about 100° C., preferably, between about 70° C. and about 80° C.

A simulated fuel cell feed stream is prepared preferably comprising:
(a) between about 10 and about 100 ppm of carbon monoxide, more preferably, between about 30 and about 40 ppm of carbon monoxide;
(b) between about 40% (by volume) and about 50% (by volume) of hydrogen;
(c) between about 14% (by volume) and about 18% (by volume) of carbon dioxide;
(d) between about 0.5% (by volume) and about 1% (by volume) of oxygen; and (e) a balance of between about 31% (by volume) and about 54% (by volume) of nitrogen.

This simulated feed stream is passed through the catalyst tube at flow rate of preferably between about 1 milliliter per minute and about 500 milliliters per minute. The simulated fuel cell feed stream preferably has a relative humidity of at least about 95%.

Optionally, the system may also include a means by which small amounts of ambient air are added to the sample gas to raise the oxygen content to sufficient levels for complete carbon monoxide oxidation without significantly disturbing the overall composition of the gas stream.

FIG. 2 shows the measured carbon monoxide concentration of the feed stream before and after directing the flow through the preferred catalyst comprising 11.6% by weight of gold deposited on $MnO_x$. (curve 8). The analyzed stream preferably comprises about 40 ppm of CO, about 0.6% (by volume) of oxygen, about 15% (by volume) of carbon dioxide, about 35% (by volume) of nitrogen, and the balance (by volume) of hydrogen. The temperature of the stream is preferably about 23° C. and the relative humidity is preferably at least 95%. The stream's preferred flow rate is about 60 milliliters per minute. The carbon monoxide measurement is made with an Andros Model 6600 portable infrared analyzer.

It can be seen from FIG. 2 that the concentration of carbon monoxide is measured as having been around 50 ppm before the introduction of the catalyst. When the catalyst is introduced (point 8(a)), the carbon monoxide is completely and rapidly eliminated and its concentration falls to around zero in a matter of seconds (point 8(b)). The temperature of the catalyst at that moment is about 70° C. When the catalyst is removed (point 8(c)), the carbon monoxide concentration immediately increases dramatically, rapidly returning to the levels observed before the introduction of the catalyst (point 8(d)).

A second experiment is performed under the same conditions but with no oxygen in the sample gas. This experiment is designed to observe the efficiency of the catalyst when water is the main or only oxidizing source for the conversion of carbon monoxide to carbon dioxide. Under such imposed anaerobic conditions, the results show that only about 60% of the carbon monoxide is removed from the feed stream.

Figure 3:
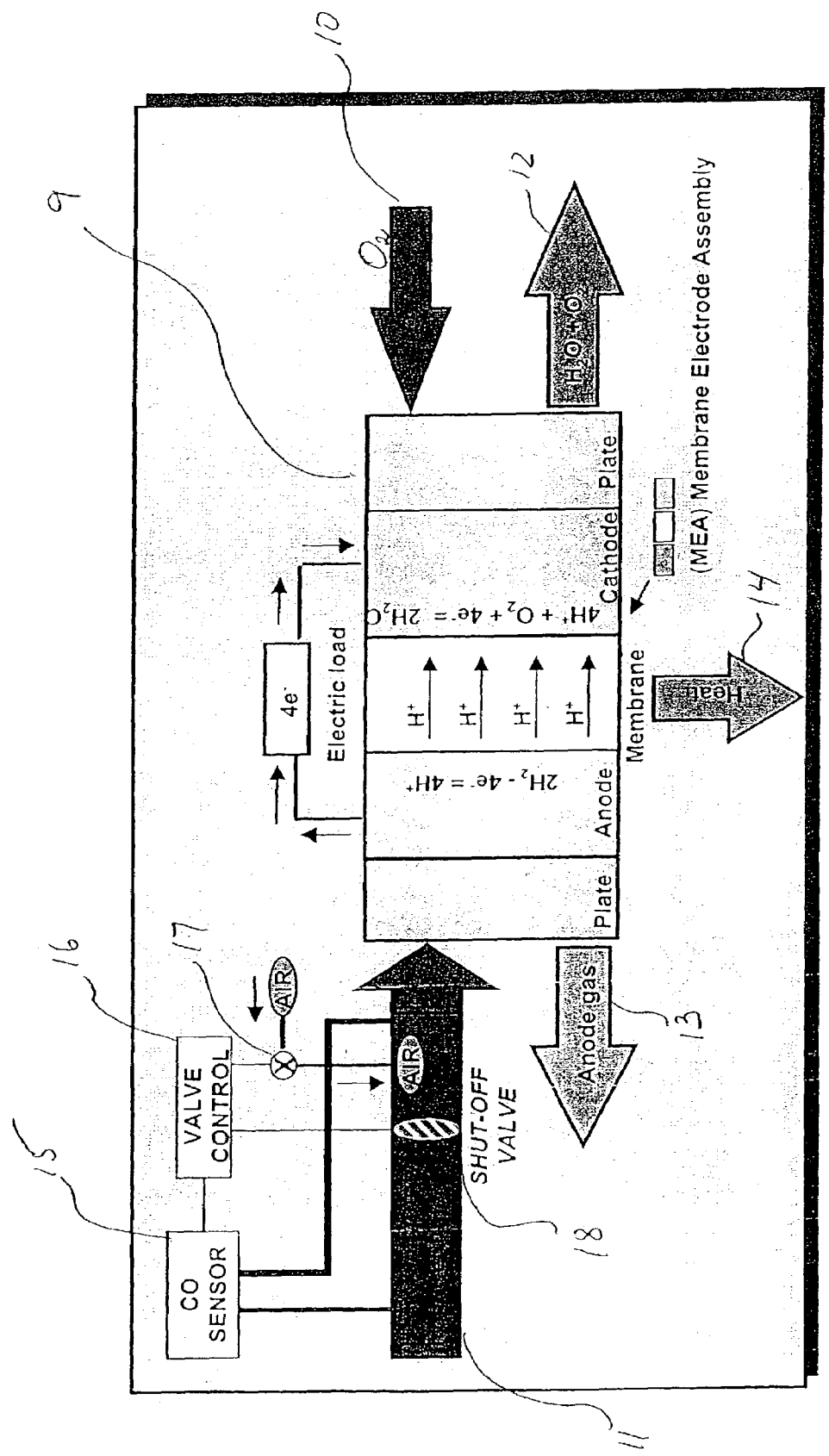
FIG. 3 is a drawing schematically showing integration of carbon monoxide sensor into a fuel cell.

FIG. 3 demonstrates how the CO sensor of this invention can be integrated into a fuel cell. The cell 9 is fed with oxygen using stream 10 and by hydrogen from a reformer using stream 11. Stream 11 comprises carbon monoxide as an impurity. The cell 9 releases a mixture of water and oxygen 12, anode gas 13, and heat 14.

The detector of this invention 15 tests the stream 11 for carbon monoxide. Too much of carbon monoxide is harmful to the cell 9 and the maximum possible amount of carbon monoxide is determined according to criteria known to those skilled in the art of fabrication and utilization of fuel cells. When the detector 15 determines that such maximum amount of carbon monoxide is reached or exceeded, the valve control system 16 either increases intake of air through valve 17 to accelerate the oxidation of carbon monoxide or cuts off the feed stream 11 utilizing the shut-off valve 18. The design of the valve control system 16, and of the valves 17 and 18 are known to those skilled in the art.

Numerous gas flow configurations utilizing the nanometer-sized gold catalysts to produce a carbon monoxide free reference gas can be designed. Modifications of the measuring process will be suggested by this disclosure to those reasonably skilled in the art. However, the important elements of this invention comprise the following:

(a) an instrument, preferably, an infrared spectroscopic instrument that is capable of making periodic zero point reference measurements; one such infrared spectroscopic instrument is the commercially available Andros Model 6600;

(b) one or more flowing gas catalyst beds, preferably comprising nanometer-sized gold supported on one or a combination of oxide hosts;

(c) a gas flow system able to direct the sample gas flow through the catalyst bed to create a reference gas for the infrared spectroscopic instrument from time to time.

Having described the invention in connection with several embodiments thereof, modification will now suggest itself to those skilled in the art. As such, the invention is not to be limited to the described embodiments except as required by the appended claims.

We claim:

1. An apparatus for detection of carbon monoxide, comprising:
   a) a pipe for feeding a gas feed stream mixture containing carbon monoxide;
   b) a quartz tube containing one or more beds of a catalyst, said gas feed stream mixture being directed through said quartz tube so as to eliminate or substantially reduce said carbon monoxide and to produce a reference gas;
   c) an instrument being capable of making periodic zero point reference measurements; and
   d) a valve for periodically directing said reference gas through said instrument and directing through a bypass not containing said catalyst and through said instrument a sample of a gas to be tested for said carbon monoxide, said valve being arranged so that substantially no gas flows through said quartz tube when said sample of gas to be tested is directed through said bypass, and so that substantially no gas flows through said bypass when said sample of gas to be tested is directed through said quartz tube;
   wherein said catalyst comprises particles of gold deposited on inorganic oxides or on inorganic hydroxides or on a combination of said oxides and hydroxides; and
   wherein said catalyst comprises about 11.6 percent by weight of gold and about 88.4 percent by weight of manganese oxide.

2. The apparatus according to claim 1, wherein the pipe contains hydrogen, nitrogen, carbon dioxide, water vapor, and carbon monoxide.

3. The apparatus according to claim 2, wherein the pipe contains a gas feed stream mixture having a relative humidity of at least 95% and further comprises between about 10 about 100 parts per million of carbon monoxide, between about 40% and about 50% by volume of hydrogen, between about 14% and about 18% by volume of carbon dioxide, between about 0.5% and about 1% by volume of oxygen, and a balance of between about 31% and about 46% by volume of nitrogen.

4. The apparatus according to claim 1, wherein said instrument is an infrared spectroscopic instrument, and wherein a concentration of said carbon monoxide in said sample is measured by said infrared spectroscopic instrument by comparing an infrared spectrum of said sample with an infrared spectrum of said reference gas.

5. The apparatus according to claim 4, wherein said instrument further comprises a portable non-dispersive infrared spectroscopic instrument.

6. The apparatus according to claim 1, further comprising a heater for heating said catalyst to a temperature within a range of between about 20° C. and about 100° C. prior to directing said gas feed stream mixture through said layer of said catalyst.

7. The apparatus according to claim 1, wherein said apparatus is installed on board of a vehicle.

8. The apparatus according to claim 1, wherein said apparatus is arranged in a fuel cell environment for detecting carbon monoxide in said fuel cell environment.

9. The apparatus according to claim 1, wherein said oxides and hydroxides are selected from the group consisting of iron oxide, nickel oxide, aluminum oxide, titanium dioxide, cobalt oxide, copper oxide, manganese oxides, magnesium hydroxide, and iron hydroxide.

10. The apparatus according to claim 1, wherein said particles of gold are deposited on said oxides and hydroxides by a process comprising a co-precipitation, a deposition-precipitation, and an impregnation.

11. The apparatus according to claim 1, further comprising a heater for heating said catalyst to a temperature within a range of between about 20° C. and about 100° C.

12. The apparatus according to claim 1, wherein said catalyst comprises particles of gold deposited on said oxides or hydroxides or combination of said oxides and hydroxides by co-precipitation, deposition-precipitation, or impregnation.

13. An apparatus for detection of carbon monoxide, comprising:
  a pipe for feeding a gas feed stream mixture containing carbon monoxide;
  a valve for periodically directing the gas feed stream mixture containing carbon monoxide through a quartz tube containing catalyst, and after switching, for directing a sample mixture containing carbon monoxide through a bypass not containing said catalyst to a spectrometer;
  the quartz tube containing one or more beds of layer of the catalyst, said gas feed stream mixture being directed through said quartz tube so as to eliminate or substantially reduce said carbon monoxide and to produce a reference gas, which goes through the spectrometer;
  the spectrometer being provided to self calibrate and memorize the spectrum of the reference gas and to take the spectrum of the sample gas and compare it with the memorized spectrum of the reference gas; and
  said valve being arranged so that substantially no gas flows through said quartz tube when said sample of gas to be tested is directed through said bypass, and so that substantially no gas flows through said bypass when said sample of gas to be tested is directed through said quartz tube;
  wherein said catalyst comprises particles of gold deposited on inorganic oxides or on inorganic hydroxides or on a combination of said oxides and hydroxides; and
  wherein said catalyst comprises about 11.6 percent by weight of gold and about 88.4 percent by weight of manganese oxide.

14. The apparatus according to claim 1 wherein the spectrometer is an infrared absorption spectrometer.

15. An apparatus for detection of carbon monoxide, comprising:
  a) a pipe for feeding a gas feed stream mixture containing carbon monoxide;
  b) a valve for periodically directing the gas feed stream mixture containing carbon monoxide through a quartz tube containing catalyst to a spectrometer, and after switching for directing a sample mixture containing carbon monoxide through a tube, which does not contain the catalyst to a spectrometer; wherein the catalyst comprises nanoparticles of gold;
  c) the quartz tube containing one or more beds of the catalyst, said gas feed stream mixture being directed through said quartz tube so as to eliminate or substantially reduce said carbon monoxide and to produce a reference gas;
  d) the tube, which does not contain a catalyst, feeding said gas feed steam mixture to provide a sample gas to be tested for said carbon monoxide; and
  e) the spectrometer self calibrating and memorizing the spectrum of the reference gas and the spectrometer taking the spectrum of the sample gas and comparing it with the memorized spectrum of the reference gas, wherein said quartz tube further contains a heater;
  wherein said catalyst comprises particles of gold deposited on inorganic oxides or on inorganic hydroxides or on a combination of said oxides and hydroxides; and
  wherein said catalyst comprises about 11.6 percent by weight of gold and about 88.4 percent by weight of manganese oxide.

16. An apparatus for detection of carbon monoxide, comprising:
  a) a pipe for feeding a gas feed stream mixture containing carbon monoxide;
  b) a valve for periodically directing the gas feed stream mixture containing carbon monoxide through a quartz tube containing catalyst to a spectrometer, and after switching for directing a sample mixture containing carbon monoxide through a tube, which does not contain the catalyst to a spectrometer; wherein the catalyst comprises nanoparticles of gold;
  c) the quartz tube containing one or more beds of the catalyst, said gas feed stream mixture being directed through said quartz tube so as to eliminate or substantially reduce said carbon monoxide and to produce a reference gas;
  d) the tube, which does not contain a catalyst, feeding said gas feed steam mixture to provide a sample gas to be tested for said carbon monoxide; and
  e) the spectrometer self calibrating and memorizing the spectrum of the reference gas and the spectrometer taking the spectrum of the sample gas and comparing it with the memorized spectrum of the reference gas, wherein said quartz tube is wrapped with heating tape;
  wherein said catalyst comprises particles of gold deposited on inorganic oxides or on inorganic hydroxides or on a combination of said oxides and hydroxides; and
  wherein said catalyst comprises about 11.6 percent by weight of gold and about 88.4 percent by weight of manganese oxide.

* * * * *